United States Patent [19]

Chicouri

[11] Patent Number: 5,167,959
[45] Date of Patent: Dec. 1, 1992

[54] LAXATIVE COMPOSITIONS AND A PROCESS FOR PRODUCING THEM

[76] Inventor: Marcel Chicouri, 174 Boulevard Saint-Germain, 75006 Paris, France

[21] Appl. No.: 608,203

[22] Filed: Nov. 2, 1990

[51] Int. Cl.⁵ ................................................ A61K 9/48
[52] U.S. Cl. .................................... 424/400; 424/439; 424/451; 424/452
[58] Field of Search ...................... 424/195.1, 489, 451, 424/452, 439, 600; 514/892

[56] References Cited

FOREIGN PATENT DOCUMENTS 2616329 12/1988 France ............................. 424/195.1
2621820 4/1989 France ............................. 424/195.1

Primary Examiner—Thurman K. Page
Attorney, Agent, or Firm—Bierman and Muserlian

[57] ABSTRACT

This invention has as a subject matter pharmaceutical compositions with laxative action characterized in that they contain as active ingredients an emollient laxative of mucilagineous character from vegetal origin and a lubrefiant laxative in the powder form, consisting of hardened microbedlets incorporating liquid paraffin in admixture or combination with one or several inert diluents or carriers.

8 Claims, No Drawings

LAXATIVE COMPOSITIONS AND A PROCESS FOR PRODUCING THEM

This invention relates to a combination of active ingredients endowed with laxative action.

It includes more particularly a pharmaceutical composition containing as active ingredients a laxative with emollient action and a lubrificating non-metabolisable laxative, in admixture or confunction with one or several inert non-toxic pharmaceutically-acceptable carrier or diluents-specifically it has as a subject malter, a fluid, powdery composition with laxative action characterized in that it contains as active ingredients, one or several mucilageous laxatives of vegetal origin and a lubrifiant laxative in the form of a powder in admixture or conjunction with inerts carriers or diluents, appropriate for the administration through digestive tract.

It is known that treatment of constipation preferably utilizes bulk laxatives which increase the volume of the alimentary bolus and hence improve the transit or osmotic laxatives which cause a pull of water in the alimentary bolus at the level of the large intestine or still but to a lessened proportion, irritant laxatives which cause an increase of the colon motility, an increase of the peristaltism and finally an increase of the speed of evacuation-Lubrefiant laxatives are also used since they facilitate the slipping of the alimentary bolus in the digestive tract and allow to overcome the disturbances bound to the dysfunctionning of the anal sphincter.

Each of these categories offers some advantage and therefore these different kinds of laxatives are scarcely associated and until yet, it seems to be better to use a mixture of one or several laxatives of the same kind. Thus the combination of several laxatives of the irritant type such as the laxative of vegetal origin based on anthraquinonic glucosides, are usually prescribed. On the contrary the combination of an irritant laxative such as DANTHRON and an osmotic laxative such as sodium docusate while more active, has been not to be recommended, due to the increased hepato-nocivity.

Moreover the combination of an emollient laxative and a lubricant laxative seemed to be difficult to realize and to utilize due to the differences in the consistency and fluidity of the lubrifiant laxative and hence, the performance of such a mixture, little appetizing.

Now it has been found that it possible to realize a homogeneous combination of a lubrifiant laxative agent in the form of a powder and of an emollient laxative agent, using the lubrifiant laxative agent in the form of microbedlets optionally hardened with a tanning agent. The liquid paraffin is thus embedded in gelatin. These microbedlets contain from 75 to 95% of liquid paraffin in a coating of gelatin optionally hardened with a tanning agent such as formol or tan. The thus-obtained microbedlets are strong enough to form a perfectly dry powder which does not allow the liquid paraffin to exude through the external enveloppe. The microbedlets may also be easily mixed to the emollient laxative also in a powdery form and so produce a wholly fluid and homogeneous powder.

The emollient laxative of vegetal origin is a mucilaginous laxative selected from the group consisting of the pulverulent extract of Ispagnhul (Plantago ovale) (Husk) and the powdered gum Guar.

The powdered gum Guar is preferably used and most preferably the micronized gum Guar whose fluidity is very great. The oil in a powdery form is mixed to the gum Guar and thus a homogenous and having a good stability mixture is thus realized.

This mixture may thereafter to be added to inert carriers such as lactose, microcrystalline cellulose, tricalcium phosphate, magnesium carbonate, colloidal silica, sodium citrate, or sodium phosphate. The thus-produced powder may also be added to palatability agents such as inositol or sorbitol, to sweetening agents such as saccharin or aspartam, to one or several flavouring agents such as Vanillin, ethylvanillin, furaneol or linalylthiol; to preservating agents such as sorbic acid, an alkali metal sorbate, ascorbic acid, sodium ascorbate or calcium ascorbate.

Moreover the use of liquid paraffin in the form of microbedlets avoid any sweating of the oil and the unpleasant digestive perturbances which may result thereform. The tolerance of this mixture is very good, the acceptability is without proportion to that of each of the active ingredients taken individually (gel of gum Guar obtained by swelling of the gum Guar as a powder or liquid paraffin oil dispersed in carboxymethyl cellulose gel).

In the pharmaceutical compositions according to this invention, the weight ratio between gum Guar or Ispaghul and the microbedlets of liquid paraffin, ranges from 10 parts for 1 part of liquid paraffin in the form of microbedlets to 1 part of Gum Guar for 2 parts of liquid paraffin.

Preferably the pharmaceutical compositions of this invention are offered in the form of sachets of powder, or packages of powder containing from 4 to 10 g of the mixture.

The powdery mixture is divided into small units or stored in bulk in glas bottles. It is intended to be poured in a definite volume of water in which gum Guar or powdery extract of Ispaghul forms a mucilage which includes the microbedlets of liquid paraffin. It is thus obtained a fluid emulsion which is perfectly pleasant to the taste, easily ingestible and of unequivalent efficiency. In fact the own effects of each of the laxative constituents of the composition according to this invention not only are mutually additive but also reciprocally they gather strength with a true synergy.

It appears from the clinical trials performed using the pharmaceutical compositions according to this invention, in contrast to gum Guar or Ispaghul, that the action of loading for Ispaghul or gum Guar is markedly strengthened and facilitated by admixing thereto a lubrificating laxative.

A most preferred composition is that which contains gum Guar and the microbedlets of liquid paraffin at equal parts. The unit of administration is that which includes 6 to 7 g of the mixture in a polyethylene bag covered with an aluminum foil. The mixture acording to the invention may also be divided into well-closed glas flasks and the administration of the mixture will be made in the form of thea-spoons with 50 to 100 ml water, while increasing very markedly the amount of extract of Ispaghul in respect of the microbedlets of liquid paraffin. A medicine the laxative properties of which are significantly lessened for the benefit of hypocholesterolemiant properties. It has been particularly stated that combinations which contain form 10 to 20 parts of extract of Ispaghul for 1 to 2 parts of microbedlets of liquid paraffin induced by repeated administrations, a noticeable decrease of the level of blood cholesterol. It appears thus in fact—without it could be the only explanation thereof—that the extract of Ispaghul by its polysaccharidic acids will be able to bind to the biliary acids and the derivatives thereof in decreasing the resorption. Through the presence of a lubrifiant laxative, they are eliminated by the digestive way. This decrease in the resorption causes a depletion in the organism into biological precursors of cholesterol and accordingly a progressive decrease of the circulating cholesterol.

This decrease of the content in liquid paraffin is also an important element, since while allowing a reel efficiency, the microbedlets of liquid paraffin in small amounts avoid the occurance of an undesirable side-effect such as the laxative effect after protracted administration.

The dosology is from 1 to 2 sachets per day for a set of time which does not exceed five days.

The pharmaceutical compositions according to this invention are useful drugs which are more particularly suitable to treat constipation, namely by the elderly, the people in the bed, the pregnant women, the women in child bed or the patients which need to be the event of surgical abdominal intervention or an intestinal radiological cliche.

This invention also relates to a process for producing laxative pharmaceutical compositions which consists in that they are realized in a first step, a powder of gum Guar or of Ispaghul by grinding the seeds of Cyamopsis tetragona hebata or psyllium, then separating of the teguments, rotative screening and inclusion with the very fine powder (Husk) added to the microbedlets of liquid paraffin until a homogenous mixture is obtained and final sieving of the mixture which is diluted with an inert carrier then sweetening and/or flavouring when desired and divided into unit dosages.

The following examples illustrate the invention. They do not limit it in any manner.

EXAMPLE I

Sachets with 6,6 g of the mixture

A powder of gum Guar is at the first time realized by forming a powder of the seeds of *Cyamopsis tetragonalobata*, separation of the tegument and sieving on a rotative 200 mesh sieve. The so screened powder which is made from the successive grindings of the seeds, is thereafter ground using a crushing-maching with beams linked to a reception cone followed by a rotative screener fitted with a screen of 400 μm width meshes.

25 kg of the thus-formed powder are then mixed with 28 kg of bedlets of liquid paraffin until obtention of a homogenous mixture. The powder is screened on a 200 sieve and the very fluid mixture is then sweetened with 0.100 g of Furaneol and 0.01 g of linalylthiol.

The mixture is thereafter divided into sachets of 6.6 g containing the mixture in equal parts of gum Guar and liquid paraffin.

Production of the microbedlets of liquid paraffin 100 ml of a 5% solution of gelatin is prepared in the cold in a container fitted with a device for strong mechanic stirring. To this solution 120.50 g of liquid paraffin are added portion wise and the stirring is maintained until a fine emulsion is obtained. The co-acervation of the droplets of gelatin is realized by adding a 25% aqueous solution of ammonium acetate. One filters to eliminate the exces of oily phase which has not been included in the gelatin. The microbedlets are thereafter suspended in a 40% solution of formaldehyde for 30 mn under strong stirring then separated and dried in an oven at a temperature lower than 40° C. The microbedlets are offered in the form of small easily fluid droplets, having a faint smell and colour-less. They are further mixed with 10% lactose and 1% talc to increase their fluidity.

Microbedlets of vaseline oil are prepared in the same fashion.

EXAMPLE II

Sachets of 10 g of the mixture gum Guar/liquid paraffin 400 g of powdered gum Guar obtained as described in example I, are mixed with 250 g of microbedlets of liquid paraffin until complete homogeneity. The mixture is successively added to 6 g microcrystalline cellulose, then 4 g colloidal silica and 55 g inositol. The whole mixture is divided into sachets of 10 g of powder. The content of a sachet is poured into half a glass of water and shaked until an easily ingestible milk is formed.

EXAMPLE III

Sachets of 6.6 g of the mixture Ispaghul/liquid paraffin

As a preliminary a powder of Ispaghul [plantago ovata (plantaginacees)] originating from India where the plant is grown. The harvest with a harvester takes place in March/April.

After treshing and winnowing, the seeds are sieved on a screen with alveoles. The teguments are separated by successive screenings (6 or 7) through a crushing machine with bullets then gauged by passes on a screen.

The screened powder, formed with successive grindings of teguments, is thereafter crushed using a crushing machine wiht beams (Promill) connected to a reception cone followed with a rotative sieving machine fitted with a screen with 400 μm mesh.

25 kg of the thus-prepared Ispaghul powder are thereafter mixed to the 28 kg of microbedlets of liquid paraffin until an homogeneous mixture is obtained. The powder is screened on a sieve 200 and the very fluid mixture is sweetened with 0.100 g sodium saccharinate and flavoured with 0.200 g orange oil. The mixture is further divided into sachets of about 6.6 g containing equal parts of mixture of Ispaghul powder (Husk) and liquid paraffin.

EXAMPLE IV

Sachets of 10 g of the mixture Ispaghul/liquid paraffin 400 g of Ispaghul powder obtained as in example I are mixed with 250 g of microbedlets of liquid paraffin until complete homogeneity. The mixture is added to 6 g tricalcium phosphate and 4 g colloidal silica (Aerosil 200). The mixture is then divided into small sachets of 10 g of powders. The content of a sachet is poured into half a glass of water and stirred to form an easily-ingestible milky preparation.

What is claimed is:

1. A laxative composition comprising a laxative effective amount of 6 to 7 g of a mixture of an emollient laxative of vegetal origin in pulverulent form selected from the group consisting of extracts of Ispaghul and guar gum and a lubrificating laxative of liquid paraffin in a gelatin coating in powder form in a weight ratio of 10:1 to 1:2 and an inert component in a polyethylene bag covered with aluminum foil.

2. A pharmaceutical composition according to claim 1 in which a mucilaginous laxative is in a form of a very fluid, screened powder, obtained by crushing and screening of a grindings of seeds of Cyamopsis tetragonalobata, previously freed of the teguments.

3. A pharmaceutical composition acording to claim 1 wherein the mucilaginous laxative is a very fine powder obtained by means of crushing and screening of the seeds of Psyllium ovata.

4. A pharmaceutical composition according to claim 1 wherein the lubrifiant laxative in the form of a powder, consists of hardened microbedlets containing liquid paraffin or vaseline oil.

5. A pharmaceutical composition according to claim 1 wherein the microbedlets contain from 75 to 95% of liquid paraffin.

6. A method of inducing laxative activity in warm-blooded animals comprising administering to warm-blooded animals a laxative effective amount of a composition of claim 1.

7. A pharmaceutical composition according to claim 1 wherein the weight ratio between powdered gum Guar and the microbedlets of oil, ranges form 10 parts for 1 part to 2 parts of powdered gum Guar to 10 parts of oil.

8. A pharmaceutical composition according to claim 1 wherein the weight ratio powder of Ispaghul/microbedlets of liquid paraffin ranges form 10 parts to 1 parts to 2 parts for 10 parts of liquid paraffin.

* * * * *